United States Patent [19]
Philippe et al.

[11] Patent Number: 6,002,038
[45] Date of Patent: Dec. 14, 1999

[54] FLUOROSILICONE COMPOUNDS IN THE FORM OF OIL AND USE OF SAME IN COSMETICS

[75] Inventors: Michel Philippe, Wissous; Jean-Christophe Henrion, Pantin, both of France

[73] Assignee: L'Oreal, Paris, France

[21] Appl. No.: 09/292,312

[22] Filed: Apr. 15, 1999

[30] Foreign Application Priority Data

Apr. 15, 1998 [FR] France ................................. 98 04682

[51] Int. Cl.$^6$ ........................................ C07F 7/10
[52] U.S. Cl. ..................... 556/420; 514/63; 624/401; 624/78.03; 624/DIG. 5
[58] Field of Search ................. 512/420; 514/63; 424/401, 78.03, DIG. 5

[56] References Cited

U.S. PATENT DOCUMENTS

| | | | |
|---|---|---|---|
| 4,900,474 | 2/1990 | Terae et al. | 252/358 |
| 5,321,108 | 6/1994 | Kunzler et al. | 526/242 |
| 5,739,369 | 4/1998 | Matsumura et al. | 556/425 |

OTHER PUBLICATIONS

Chemical Abstracts, Sep. 16, 1996, vol. 125, No. 12, Abstract No. 146902, Hirofumi Kondo, "Lubricants and magnetic recording media using them", XP002086437.

Chemical Abstracts, Jan. 14, 1991, vol. 114, No. 2, Abstract No. 8284, Susumu Kawakami et al, "Formation of fluorosiloxane coatings using the Langmuir–Blodgett technique", XP002086438.

*Primary Examiner*—Paul F. Shaver
*Attorney, Agent, or Firm*—Oblon, Spivak, McClelland, Maier & Neustadt, P.C.

[57] ABSTRACT

Flouorosilicone compounds of formula (I):

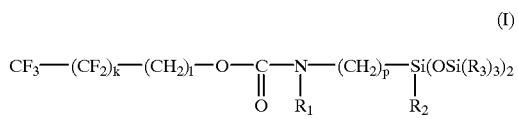

wherein k is 1–17, l is 1–18, p is 1–6, $R_1$ represents a hydrogen atom or a $C_1$–$C_6$ alkyl group, $R_2$ represents a $C_1$–$C_6$ alkyl group or the —$OSi(R_3)_3$ group, and $R_3$ represents a $C_1$–$C_4$ alkyl group.

These are applicable, in the form of non-volatile oil, for topical application in field of cosmetics and dermatology.

14 Claims, No Drawings

FLUOROSILICONE COMPOUNDS IN THE FORM OF OIL AND USE OF SAME IN COSMETICS

BACKGROUND OF THE INVENTION

1. Field of the Invention

The present invention relates to a fluorosilicone compound, which is a non-volatile oil and to the use of same in the fields of cosmetics and dermatology, more particularly to use in make-ups or skin-care products.

2. Description of the Background

The use of new oils in cosmetic and dermatological preparations which are capable of improving the properties of the cosmetic or dermatological compositions has received special investigative attention from the viewpoint, in particular, of improving the consistency and ease of application of the compositions.

In addition, the oils used in such applications must inherently have good properties which make it possible to impart greater suppleness and a pleasant feel to the skin.

A great number of oils already have been proposed and are commonly used in cosmetics for the preparation of various make-up products. Among these oils, two large classes have been developed and have been widely employed in cosmetics in recent years. They are the silicone oils on the one hand and the fluorinated oils on the other.

Some of these oils, however, have the major disadvantage that they are not compatible with other oils or fatty substances employed in cosmetics or dermatology. This problem of compatibility is of paramount importance from the viewpoint of obtaining compositions which have good homogeneity.

After various studies on a large number of compounds, it has been discovered that a particular class of fluorosilicone compounds is highly compatible with various oils, especially of the hydrocarbon, perfluorinated and/or silicone types.

The state of the art relative to fluorosilicone compounds is represented substantially by Japanese Patent Application JP 06-256756, which describes, in water-repellent compositions for the treatment of glass, ceramic and metal surfaces, the use of fluorosilicone compounds of the formula:

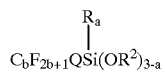

in which:

$R_1$ and $R_2$ are monovalent $C_1$–$C_4$ hydrocarbon groups,
Q is a divalent $C_2$–$C_{10}$ organic group,
a is 0 or 1, and
b is 1–12.

SUMMARY OF THE INVENTION

Accordingly, one object of the present invention is to provide fluorosilicone compounds. which, as oils, are compatible with other oils and fatty commonly employed in cosmetic and dermatological compositions.

Briefly, this object and other objects of the present invention as hereinafter will become more readily apparent can be attained by a fluorosilicone compound of the formula (I):

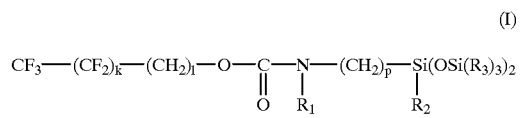

wherein:
k is 1–17, l is 1–18, p is 1–6,
$R_1$ represents a hydrogen atom or a $C_1$–$C_6$ alkyl radical,
$R_2$ represents a $C_1$–$C_6$ alkyl radical or the —OSi($R_3$)$_3$ radical, and $R_3$ represents a $C_1$–$C_4$ alkyl radical.

DETAILED DESCRIPTION OF THE PREFERRED EMBODIMENTS

In formula (I) above, the $C_1$–$C_4$ and $C_1$–$C_6$ alkyl radicals are preferably selected from the group consisting of methyl, ethyl, propyl, isopropyl, butyl, tert-butyl, and hexyl radicals.

Among the compounds within the scope of formula (I) which are of particular interest are:

N-(2-F-octylethyloxycarbonyl)-3-aminopropylbis(trimethylsiloxy)methylsilane,

N-(2-F-hexylethyloxycarbonyl)-3-aminopropylbis(trimethylsiloxy)methylsilane,

N-(2-F-butylethyloxycarbonyl)-3-aminopropylbis(trimethylsiloxy)methylsilane,

N-(2-F-octylethyloxycarbonyl)-3-aminopropyltris(trimethylsiloxy)silane,

N-(2-F-hexylethyloxycarbonyl)-3-aminopropyltris(trimethylsiloxy)silane, and

N-(2-butylethyloxycarbonyl)-3-aminopropyltris(trimethylsiloxy)silane.

Another aspect of the present invention is the preparation of the compound of formula (I), which process comprises reacting, in an organic solvent, a chloroformate of formula (II):

with an aminosiloxane of formula (III):

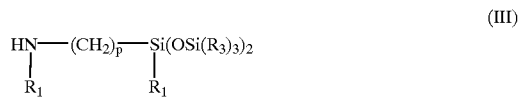

in the presence of a basic aqueous solution having a pH in the range of 8–12, preferably 10–11.

The condensation reaction is preferably conducted at room temperature with agitation. After the end of the reaction and addition of water, the mixture is acidified, decanted and dried. After evaporation of the solvent, distillation produces a colorless, odorless oil.

The present invention also has, as an object, a composition suitable for topical application, especially a cosmetic or dermatological composition containing, in the form of oil, at least one fluorosilicone compound of formula (I) such as defined hereinabove.

In the composition of the invention, the fluorosilicone compound is generally present in a proportion of from 1–95 wt %, preferably 5–80 wt %, and in the best case 5–60 wt % relative to the total weight of the composition.

As mentioned hereinabove, the oily fluorosilicone compound of the invention is very excellently compatible with a large number of oils, especially the hydrocarbon oils, and the perfluorinated and/or silicone oils. Suitable such oils include, in particular, paraffin oil, vaseline oil, isododecane, isohexadecane, the polyisobutenes, the hydrogenated polyisobutenes, the triglycerides of capric and caprylic acid, the cyclomethicones (especially the $C_5$ class), olive oil, octyldodecanol, perfluorodecalin, perfluorophenanthrene, the perfluorocycloalkyl compounds, perfluorodecalin, perfluorophenanthrene, the perfluorocycloalkyl compounds and the perfluoropolyethers.

Suitable perfluorocycloalkyl compounds include, in particular, those of formula (IV):

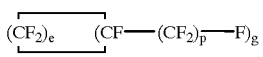
(IV)

in which:
e is 4 or 5, g is 1 or 2, and p is 1, 2 or 3;
with the proviso that, when g=2, the groups are not necessarily in the alpha position relative to each other.

Among perfluoropolyethers, included, in particular, are those of formulas (V) and (VI):

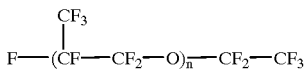
(V)

in which:
n is 7–30; and

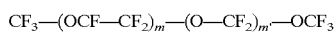
(VI)

wherein the ratio m/m' is from 20–40.

Suitable perfluoropolyethers included among those of formulas (V) and (VI), are especially those sold under the name of "FLUORTRESS LM 36®" by the DUPONT Company, and those sold under the name of "FOMBLIN" by the MONTFLUOS Company, such as FOMBLIN HCR®".

The mixtures of oily fluorosilicone compound of the invention and hydrocarbon, perfluorinated and/or silicone oil, possibly together with other fatty substances, can advantageously constitute the fatty phase of various cosmetic compositions, which may be anhydrous or aqueous.

In compositions of the anhydrous type, such can have the form of an anhydrous gel, of a stick such as lipstick or concealer, or the form of an anhydrous compact such as a color base or foundation, an eye shadow, a blush, an eye liner or mascara, a body make-up or even loose powder. In this case, the fluorosilicone compound of the invention functions as binder, alone or in a mixture with other oils.

In the compositions of the aqueous type, such are dispersions in the form of a water-in-oil (W/O) or an oil-in-water (O/W) emulsion, which substantially comprise (i) a fatty phase, (ii) an aqueous phase and (iii) at least one emulsifying agent. These compositions can also have the form of an oil-in-water dispersion by virtue of lipid cells. These compositions then have the appearance of a white or tinted cream or milk (such as a liquid color base).

Of course, the compositions of the invention can contain any type of conventional cosmetic or dermatological ingredient used in the fields in question such as preservatives, perfumes, fillers, coloring agents, pigments, gelling agents, waxes and cosmetic or dermatological active principles.

Having generally described this invention, a further understanding can be obtained by reference to certain specific examples which are provided herein for purposes of illustration only and are not intended to be limiting unless otherwise specified.

EXAMPLES OF PREPARATION

Preparation of N-(2-F-octylethyloxycarbonyl)-3-aminopropylbis(trimethylsiloxy)methylsilane In a 1-liter reactor equipped with two dropping funnels attached to its top there is introduced 50 g (95 mmol) of 2-F-octylethyl chloroformate dissolved in 250 ml of acetone. After agitation of the mixture a room temperature, the solutions A and B defined hereinbelow are introduced dropwise and simultaneously in 1 hour by means of two funnels, such that the pH of the reaction mixture is between 10 and 11.

Solution A
26.56 g (95 mmol) of 3-aminopropylbis(trimethylsiloxy)methylsilane in 100 ml of acetone.

Solution B
47.5 ml of 2 N aqueous sodium hydroxide solution.

After introduction of solutions A and B into the reactor, agitation is continued for one more hour at room temperature, afer which 400 ml of water and 200 ml of dichloroethane are added to the reaction mixture, which is then acidified slowly to pH=2 by addition of concentrated HCl.

After decantation, the organic phase is recovered, washed and dried over sodium sulfate.

The solvent is then evaporated and the raw oil obtained is distilled under reduced pressure to yield 27.1 g of N-(2-F-octylethyloxycarbonyl)-3-aminopropylbis(trimethylsiloxy)methylsilane in the form of a colorless, odorless oil.

Analyses
Boiling point: 135–135.5° C. at 0.40–0.45 mbar
$^1$H NMR (CDCl$_3$) in agreement with the structure
GC: single peak
Elemental Analysis

|  | C | H | O | N | F | Si |
|---|---|---|---|---|---|---|
| Calc. | 32.77 | 4.19 | 8.31 | 1.82 | 41.96 | 10.95 |
| Theoretical | 32.70 | 4.15 | — | 1.77 | 42.60 | 11.26 |

Preparation of the Other Fluorosilicone Compounds
The same procedure as described hereinabove was used to prepare the different silane compounds listed above in the form of a colorless, odorless oil.

COSMETIC COMPOSITIONS

Example 1
Color Base or Foundation in the Form of a Stick
A color base in the form of a stick within the scope of the invention is prepared by mixing the following ingredients:

| | |
|---|---|
| 2-F-Octylethyl dodecan-1,12-dioate | 30 g |
| N-(2-F-Octylethyloxycarbonyl)-3-aminopropylbis-(trimethylsiloxy)methylsilane | 60 g |
| Pigments | 10 g |

The fluorosilicone compound of this color base can be advantageously replaced by any one of the compounds listed on pages 2 and 3.

Example 2
Care Cream (Water-in-oil Emulsion)

| | |
|---|---|
| N-(2-F-Octylethyloxycarbonyl)-3-aminopropylbis-(trimethylsiloxy)methylsilane | 10 g |
| Trifluoromethyl $C_1$–$C_4$ alkyldimethicone (Shin Etsu) | 12 g |
| Triperfluoroalkylethyl citrate (Zonyl TBC of Dupont de Nemours) | 8 g |
| Cetyldimethicone copolyol (Abil WE09 of Goldschmidt) | 5 g |
| Salt | 0.7 g |
| Water | made up to 100 g |

The disclosure of French priority Application Number 98/04682 filed Apr. 15, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A fluorosilicone compound of formula (I):

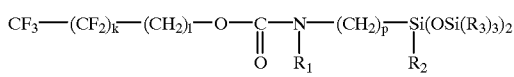

(I)

wherein k is 1–17, l is 1–18, p is 1–6, $R_1$ represents a hydrogen atom or a $C_1$–$C_6$ alkyl radical, $R_2$ represents a $C_1$–$C_6$ alkyl radical or the —$OSi(R_3)_3$ radical, and $R_3$ represents a $C_1$–$C_4$ alkyl radical.

2. The compound according to claim 1, wherein the alkyl radicals of groups $R_1$ and $R_2$ are selected from the group consisting of methyl, ethyl, propyl, isopropyl, butyl, tert-butyl and hexyl radicals.

3. The compound according to claim 1, wherein the alkyl radicals of group $R_3$ are selected from the group consisting of methyl, ethyl, propyl, isopropyl, butyl, and tert-butyl. radicals.

4. The compound according to claim 1, wherein the fluorosilicone compound is a member selected from the group consisting of:

N-(2-F-octylethyloxycarbonyl)-3-aminopropylbis(trimethylsiloxy)methylsilane,

N-(2-F-hexylethyloxycarbonyl)-3-aminopropylbis(trimethylsiloxy)methylsilane,

N-(2-F-butylethyloxycarbonyl)-3-aminopropylbis(trimethylsiloxy)methylsilane,

N-(2-F-octylethyloxycarbonyl)-3-aminopropyltris(trimethylsiloxy)silane,

N-(2-F-hexylethyloxycarbonyl)-3-aminopropyltris(trimethylsiloxy)silane, and

N-(2-butylethyloxycarbonyl)-3-aminopropyltris(trimethylsiloxy)silane.

5. A process for preparing a fluorosilicone compound of formula (I) of claim 1, which comprises:

reacting, in an organic solvent, a chloroformate of formula (II):

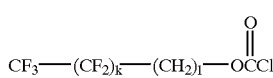

(II)

with an aminosiloxane of formula (III):

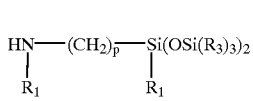

(III)

wherein k, l, p, $R_1$, $R_2$ and $R_3$ are as defined above, in the presence of an aqueous basic solution.

6. The process according to claim 5, wherein the pH of the reaction mixture ranges from 8–12.

7. A composition for topical application, which comprises:

in the form of an oil, at least one fluorosilicone compound of formula (I) as defined in claim 1.

8. The composition according to claim 7, wherein the fluorosilicone compound is present in an amount of 1–95 wt % relative to the total weight of the composition.

9. The composition according to claim 8, wherein said amount of fluorosilicone compound ranges from 5–80 wt % relative to the total weight of the composition.

10. The composition according to claim 9, wherein said amount of fluorosilicone compound ranges from 5–60 wt % relative to the total weight of the composition.

11. The composition according to claim 7, wherein the fluorosilicone compound is present in the form of a mixture with at least one hydrocarbon, perfluorinated and/or silicon oil.

12. The composition according to claim 11, wherein said at least one hydrocarbon, perfluorinated and/or silicon oil is a member selected from the group consisting of paraffin oil, vaseline, isododecane, isohexadecane, the polyisobutenes, the hydrogenated polyisobutenes, the triglycerides of capric and caprylic acid, the cyclomethicones, olive oil, octyldodecanol, perfluorodecalin, perfluorophenanthrene, the perfluorocycloalkyl compounds, perfluorodecalin, perfluorophenanthrene, the perfluorocycloalkyl compounds and the perfluoropolyethers.

13. The composition according to claim 7, wherein the composition is anhydrous and is manufactured in the form of a stick, a compact, a mascara, a gel or an eye liner.

14. The composition according to claim 7, wherein the composition is an aqueous formulation in the form of a water-in-oil or an oil-in-water emulsion, or of an oil-in-water dispersion which contains lipid cells or droplets.

* * * * *